US011554129B2

(12) United States Patent
Kim et al.

(10) Patent No.: US 11,554,129 B2
(45) Date of Patent: Jan. 17, 2023

(54) COMPOSITION FOR TREATING CHRONIC RENAL TRANSPLANT DYSFUNCTION COMPRISING BISPHOSPHONATE

(71) Applicant: INDUSTRY-ACADEMIC COOPERATION FOUNDATION, YONSEI UNIVERSITY, Seoul (KR)

(72) Inventors: Beom Seok Kim, Seoul (KR); Seung Hwan Song, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 12 days.

(21) Appl. No.: 16/604,766

(22) PCT Filed: Apr. 13, 2018

(86) PCT No.: PCT/KR2018/004360
§ 371 (c)(1),
(2) Date: Oct. 11, 2019

(87) PCT Pub. No.: WO2018/190685
PCT Pub. Date: Oct. 18, 2018

(65) Prior Publication Data
US 2020/0101092 A1 Apr. 2, 2020

(30) Foreign Application Priority Data
Apr. 14, 2017 (KR) .......................... 10-2017-0048564

(51) Int. Cl.
*A61K 31/675* (2006.01)
*A23L 33/10* (2016.01)
*A61K 31/663* (2006.01)

(52) U.S. Cl.
CPC ............ *A61K 31/675* (2013.01); *A23L 33/10* (2016.08); *A61K 31/663* (2013.01)

(58) Field of Classification Search
CPC ...... A61K 31/663; A61K 31/675; A23L 33/10
See application file for complete search history.

(56) References Cited

FOREIGN PATENT DOCUMENTS

| JP | 2005-530819 A | 10/2005 |
| KR | 2001-0020838 A | 3/2001 |
| KR | 10-0864743 B1 | 10/2008 |
| WO | 01/97788 A2 | 12/2001 |
| WO | 2004/052408 A1 | 6/2004 |
| WO | 2017/210611 A1 | 12/2017 |

OTHER PUBLICATIONS

Liu, Chia-Yuan, M.D., et al. "Zoledronic acid, an amino-bisphosphonate, prolongs survival of skin allografts." Clin. Invest Med. (2012), vol. 35, Issue 4, pp. E165-E172. (Year: 2012).*
Torres, P., et al. "Changes in Cytokine mRNA Levels in Experimental Corneal Allografts after Local Clodronate-Liposome Treatment." Investigative Ophthalmology & Visual Science. (Dec. 1999), vol. 40, No. 13, pp. 3194-3201. (Year: 1999).*
Muratore, M., et al. "Clinical utility of clodronate in the prevention and management of osteoporosis in patients intolerant of oral bisphosphonates." Drug Design, Development and Therapy. (2011), vol. 5, pp. 445-454. (Year: 2011).*
International Search Report dated Aug. 3, 2018 from the Korean Intellectual Property Office in Application No. PCT/KR2018/004360.
Extended European Search Report dated Dec. 3, 2020 from the European Patent Office in Application No. 18784636.5.
Stephanie M. Toth-Manikowski et al., "Outcomes of bisphosphonate therapy in kidney transplant receipients: a systematic review and meta-analysis", Clinical Transplantation, 2016, vol. 30, pp. 1090-1096 (8 pages total).
Nigel D. Toussaint et al., "Bisphosphonates in Chronic Kidney Disease; Balancing Potential Benefits and Adverse Effects on Bone and Soft Tissue", Clinical Journal of the American Society of Nephrology, 2009, vol. 4, pp. 221-233 (14 pages total).
Thomas Jakobsen MD, PhD. et al., "The Effect of Soaking Allograft in Bisphosphonate: A Pilot Doese-response Study", Clinical Orthopaedics and Related Research, Sep. 18, 2009, vol. 468, No. 3, pp. 867-874 (8 pages total).
Sally Lee et al., "Pamidronate used to attenuate post-renal transplant bone loss is not asociated with renal dysfunction", Nephrology Dialysis Transplantation, Oct. 10, 2004, vol. 19, No. 11, pp. 2870-2873 (4 pages total).
Chia-Yuan Liu, MD et al., "Zoledronic acid, an amino-bisphosphonate, prolongs survival of skin allografts", Aug. 4, 2012, vol. 35, No. 4 pp. E165-E172 (8 pages total).
Drew D. Moore, MD et al., "Effect of Bisphosphonate Pretreatment on Fresh Osteochondral Allografts: Analysis of In Vitro Graft Structure and In Vivo Osseous Incorporation", Orthopedics, 2018, vol. 41, No. 3, pp. e376-e382 (7 pages total).
Hazim Sadideen et al., "Mineral and bone disorder after renal transplantation: a review", International Urology and Nephrology, Dec. 18, 2007, vol. 40, pp. 171-184 (14 pages total).
Tanja P.A.M. Slegers et al., "Effect of local macrophage depletion on cellular immunity and tolerance evoked by corneal allografts", Current Eye Research, Jan. 2, 2003, vol. 26, No. 2, pp. 73-79 (7 pages total).
Journal, 2004, vol. 46, No. 7, pp. 667-675.

(Continued)

*Primary Examiner* — Timothy R Rozof
(74) *Attorney, Agent, or Firm* — Sughrue Mion, PLLC

(57) ABSTRACT

The present invention relates to a composition for preventing or treating chronic allograft dysfunction, comprising bisphosphonate which is used as a therapeutic agent for osteoporosis. The composition for preventing or treating chronic allograft dysfunction, comprising bisphosphonate, according to the present invention has an excellent prophylactic and/or therapeutic effect on chronic allograft dysfunction caused by a gradual decrease in the function of a transplanted tissue or organ which occurs after tissue or organ transplantation surgery, and thus is expected to be able to remarkably increase a long-term survival after transplantation surgery.

4 Claims, 3 Drawing Sheets

(56) References Cited

OTHER PUBLICATIONS

Glen S. Markowitz et al.; Toxic acute tubular necrosis following treatment with zoledronate (Zometa); Kidney International, 2003, vol. 64; pp. 281-289.
Notification of Reasons for Refusal dated Mar. 11, 2022 from the Japanese Intellectual Property Office in related Japanese Patent Application No. 2019-555020.

* cited by examiner

[FIG. 1]
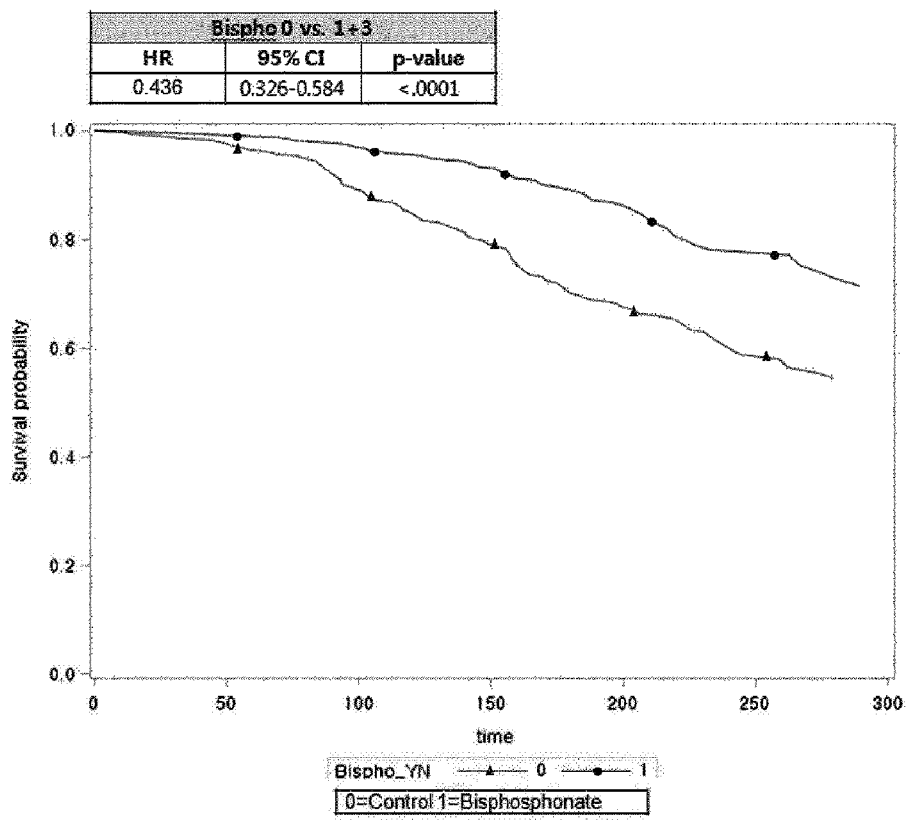
[FIG. 2]
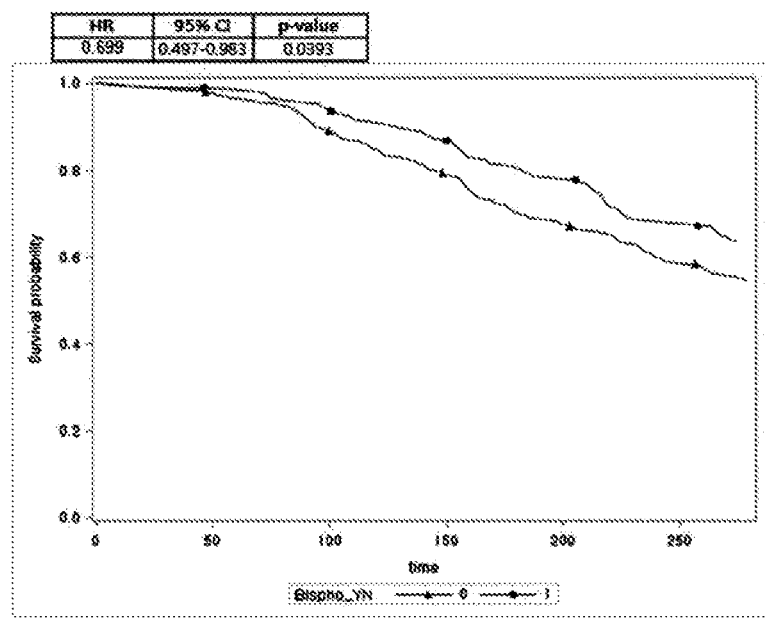

[FIG. 3]
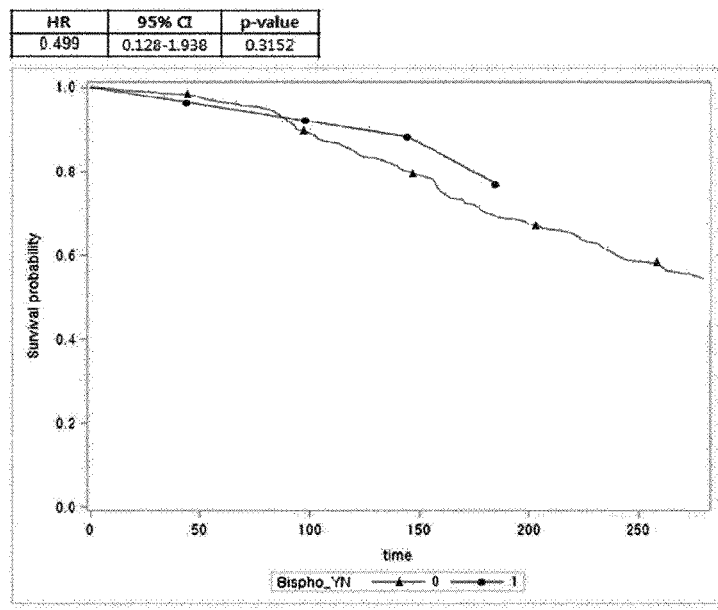
[FIG. 4]
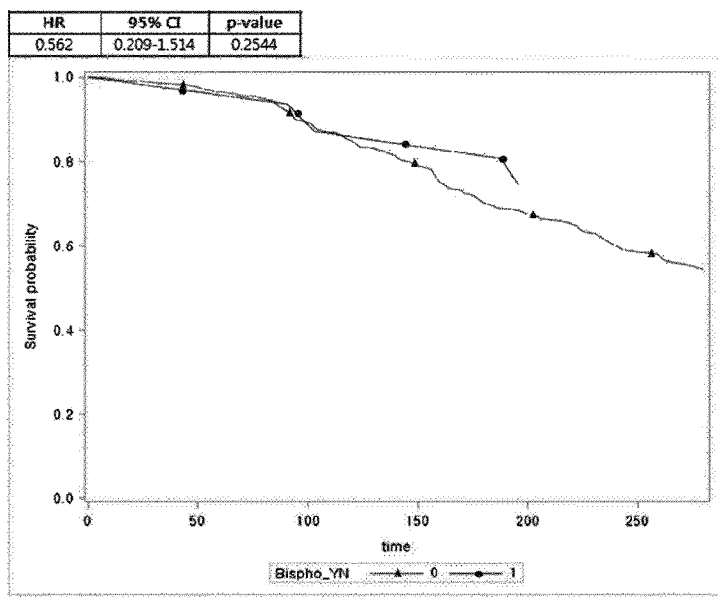

[FIG. 5]
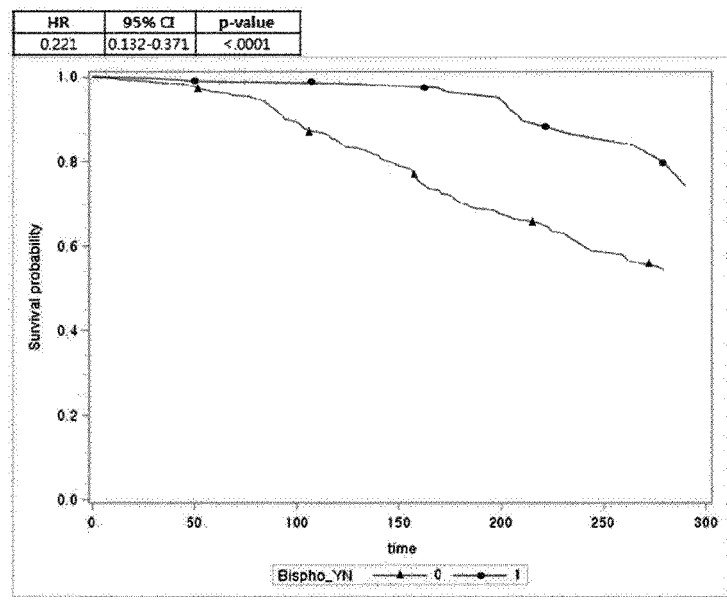
[FIG. 6]
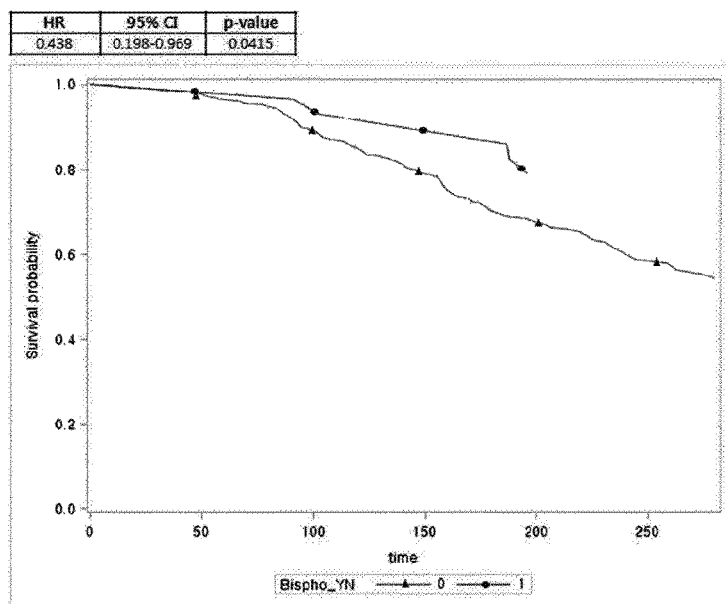

COMPOSITION FOR TREATING CHRONIC RENAL TRANSPLANT DYSFUNCTION COMPRISING BISPHOSPHONATE

CROSS REFERENCE TO RELATED APPLICATIONS

This application is a National Stage of International Application No. PCT/KR2018/004360 filed Apr. 13, 2018, claiming priority based on Korean Patent Application No. 10-2017-0048564 filed Apr. 14, 2017, the entire disclosures of which are incorporated herein by reference.

TECHNICAL FIELD

The present invention relates to a composition for preventing or treating chronic allograft dysfunction, comprising bisphosphonate which is used as a therapeutic agent for osteoporosis.

BACKGROUND ART

A state of kidney damage or reduced kidney function which lasts more than three months is called chronic kidney disease. In this case, continuous hemodialysis or peritoneal dialysis is required, and kidney transplantation is needed for the treatment thereof. In a case of such organ transplantation, kidney function often deteriorates again due to allograft dysfunction caused after transplantation surgery. Allograft dysfunction is a type of rejection reaction in organ transplantation, which may develop from several months after transplantation. In a case where allograft dysfunction occurs, the function of the transplanted kidney is reduced, and thus there is a need to receive again continuous peritoneal dialysis or hemodialysis.

Such allograft dysfunction is largely divided into acute allograft dysfunction and chronic allograft dysfunction (Ryan J. G. et. al., *Med. Cli. N. Am.* (2016) 100: 487-503). The acute allograft dysfunction occurs within 6 months after surgery, with symptoms such as hyperacute rejection, thrombosis, urine leak, and ureteral obstruction. Mass administration of an immunosuppressive agent such as adrenocortical hormone is used as a therapeutic method therefor. However, the chronic allograft dysfunction, which occurs slowly from months to years after surgery, is rarely treated with mass administration of an immunosuppressive agent. Thus, in the United States, one-year survival is 96%, but a long-term survival after kidney transplantation is sharply decreasing with 81% of 5-year survival and 59% of 10-year survival. However, development of effective therapeutic agents therefor is insufficient (USRDS data, 2009). Accordingly, development of effective therapeutic or prophylactic agents for chronic allograft dysfunction is expected to be able to remarkably increase long-term survival probabilities of kidney transplant patients (Leonardo V. R. et. al., *Transplantation Rev.* (2016) in press).

Technical Problem

The present invention has been made to solve the above-mentioned problems in the prior art. An object of the present invention is to provide a pharmaceutical composition for preventing or treating chronic allograft dysfunction, comprising bisphosphonate as an active ingredient.

However, the technical problem to be solved by the present invention is not limited to the above-mentioned problems, and other problems which are not mentioned will be clearly understood by those skilled in the art from the following description.

Solution to Problem

Hereinafter, various embodiments described herein are described with reference to the drawings. In the following description, for thorough understanding of the present invention, various specific details are set forth, such as specific configurations, compositions, processes, and the like. However, certain embodiments may be practiced without one or more of these specific details, or in combination with other known methods and configurations. In other instances, known processes and preparation techniques have not been described in particular detail in order not to unnecessarily obscure the present invention. Reference throughout this specification to "one embodiment" or "an embodiment" means that a particular feature, configuration, composition, or characteristic described in connection with the embodiment is included in one or more embodiments of the present invention. Thus, the appearances of the phrase "in one embodiment" or "an embodiment" in various places throughout this specification are not necessarily referring to the same embodiment of the present invention. Additionally, the particular features, configurations, compositions, or characteristics may be combined in any suitable manner in one or more embodiments.

Unless otherwise specified in the specification, all the scientific and technical terms used in the specification have the same meanings as commonly understood by those skilled in the technical field to which the present invention pertains.

As used herein, the term "chronic allograft dysfunction" collectively refers to a gradual decrease in the function of a transplanted tissue or organ which occurs after tissue or organ transplantation surgery, and preferably means development of allograft dysfunction 6 months or longer after the transplantation surgery. However, the term is not limited thereto unless the function is acutely decreased. The tissue or organ may be preferably kidney, bone marrow, heart, cornea, intestine, liver, lung, pancreas, skin, or the like, with kidney being more preferable. However, the tissue or organ is not limited thereto as long as the tissue or organ is transplantable.

As used herein, the term "bisphosphonate" collectively refers to compounds which are structural analogues of pyrophosphate, with the P-O-P-group of the pyrophosphate being replaced by an enzymatically stable P-C-P-group. Substitution of hydrogen atoms at C-atoms of the P-C-P-group makes it possible to prepare bisphosphonates having various structural elements and characteristics. Known bisphosphonates approved for clinical use include pamidronate, alendronate, etidronate, clodronate, risedronate, tiludronate, ibandronate, incadronate, minodronate, olpadronate, neridronate, EB-1053, and the like, and such bisphosphonates are widely known and used as therapeutic agents for osteoporosis.

The present invention provides a pharmaceutical composition for preventing or treating chronic allograft dysfunction, comprising bisphosphonate as an active ingredient.

In an embodiment of the present invention, the bisphosphonate is preferably used for the treatment of osteoporosis, and is more preferably risedronate (risedronic acid), ibandronate (ibandronic acid), etidronate (etidronic acid), alendronate (alendronic acid), pamidronate (pamidronic acid), clodronate (clodronic acid), tiludronate (tiludronic acid), incadronate (incadronic acid), minodronate (minodronic acid), olpadronate (olpadronic acid), neridronate (neridronic acid), EB-1053, or the like, with risedronate (risedronic acid), ibandronate (ibandronic acid), etidronate (etidronic acid), alendronate (alendronic acid), and pamidronate (pamidronic acid) being even more preferable. However, the bisphosphonate is not limited thereto as long as the bisphosphonate is used for the treatment of osteoporosis.

In another embodiment of the present invention, the allograft dysfunction is an adverse effect caused by transplantation of any tissue or organ selected from the group consisting of kidney, bone marrow, heart, cornea, intestine, liver, lung, pancreas, skin, and the like, and means a gradual decrease in the function of a transplanted tissue or organ after transplantation surgery.

In yet another embodiment of the present invention, the pharmaceutical composition increases a long-term survival of 10 years or longer after transplantation surgery, and the pharmaceutical composition may be formulated in various forms including suspensions, powders, granules, tablets, sustained release preparations, injections, ointments, eye drops, and the like.

In the present invention, the pharmaceutical composition may be characterized by being in the form of capsules, tablets, granules, injections, ointments, powders, or beverages, and the pharmaceutical composition may be characterized by being targeted to humans. The pharmaceutical composition may be formulated in the form of oral preparations such as powders, granules, capsules, tablets, and aqueous suspensions, preparations for external use, suppositories, and sterile injectable solutions, respectively, according to conventional methods, and used. However, the pharmaceutical composition is not limited thereto. The pharmaceutical composition of the present invention may further comprise a pharmaceutically acceptable carrier. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration. The preparations of the pharmaceutical composition of the present invention may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms. Alternatively, the pharmaceutical composition may be formulated into solutions, suspensions, tablets, capsules, sustained-release preparations, or the like.

Meanwhile, as examples of carriers, diluents, or excipients suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a fragrance, an emulsifier, a preservative, and the like may further be included.

The route of administration of the pharmaceutical composition of the present invention includes, but is not limited to, oral, intravenous, intramuscular, intraarterial, intramedullary, intradural, intracardiac, transdermal, subcutaneous, intraperitoneal, intranasal, intestinal, topical, sublingual, or rectal route. Oral or parenteral administration is preferred. As used herein, the term "parenteral" includes subcutaneous, intradermal, intravenous, intramuscular, intraarticular, intrabursal, intrasternal, intradural, intralesional, and intracranial injection or infusion techniques. The pharmaceutical composition of the present invention may also be administered in the form of suppositories for rectal administration.

The pharmaceutical composition of the present invention may vary depending on a variety of factors, including activity of a certain compound used, the patient's age, body weight, general health status, sex, diet, time of administration, route of administration, rate of excretion, drug combination, and severity of a certain disease to be prevented or treated. A dose of the pharmaceutical composition may vary depending on the patient's condition, body weight, severity of disease, drug form, route of administration, and duration, and may be appropriately selected by those skilled in the art. The pharmaceutical composition may be administered in an amount of 0.0001 to 50 mg/kg or 0.001 to 50 mg/kg, per day. Administration may be made once a day or several times a day. The dose is not intended to limit the scope of the invention in any way. The pharmaceutical composition according to the present invention may be formulated in the form of pills, sugar-coated tablets, capsules, liquids, gels, syrups, slurries, or suspensions.

In addition, the present invention provides a food composition for preventing or ameliorating chronic allograft dysfunction, comprising bisphosphonate as an active ingredient.

In an embodiment of the present invention, the bisphosphonate is preferably used for the treatment of osteoporosis, and is more preferably any one or more selected from the group risedronate (risedronic acid), ibandronate (ibandronic acid), etidronate (etidronic acid), alendronate (alendronic acid), pamidronate (pamidronic acid), clodronate (clodronic acid), tiludronate (tiludronic acid), incadronate (incadronic acid), minodronate (minodronic acid), olpadronate (olpadronic acid), neridronate (neridronic acid), EB-1053, and the like. However, the bisphosphonate is not limited thereto as long as the bisphosphonate is used for the treatment of osteoporosis.

In still yet another embodiment of the present invention, the allograft dysfunction is an adverse effect caused by transplantation of any tissue or organ selected from the group consisting of kidney, bone marrow, heart, cornea, intestine, liver, lung, pancreas, skin, and the like, and means a gradual decrease in the function of a transplanted tissue or organ after transplantation surgery.

In still yet another embodiment of the present invention, the food composition increases a long-term survival after transplantation surgery, and may be formulated in the form of capsules, tablets, granules, powders, beverages, or the like.

In the present invention, the food composition may be used in various foods, for example, beverages, gums, teas, vitamin complexes, health supplements, and the like, and may be used in the form of pills, powders, granules, infusions, tablets, capsules, or beverages. Here, for an amount of the bisphosphonate in the food or beverage, the bisphosphonate may be added, in general, in an amount of 0.01 to 15% by weight of the total food weight in a case of the food composition of the present invention, and may be added in an amount corresponding to a proportion of 0.02 to 10 g, and preferably 0.3 to 1 g based on 100 mL in a case of a health beverage composition.

The food composition of the present invention may further comprise food additives conventional in the art, such as flavoring agents, flavors, coloring agents, fillers, and stabilizers. In the food composition according to the present invention, there is no particular limitation on ingredients added in addition to the bisphosphonate as an essential ingredient, and the food composition may contain, as additional ingredients, various flavoring agents or natural carbohydrates, or the like, as in conventional foods. Examples of the natural carbohydrate include conventional sugars including monosaccharides such as glucose and fructose; disaccharides such as maltose and sucrose; polysaccharides such as dextrin and cyclodextrin; and the like, and sugar alcohols including xylitol, sorbitol, erythritol, and the like. As flavoring agents other than those mentioned above, natural flavoring agents (thaumatin, stevia extract (for example, rebaudioside A and glycyrrhizin)) and synthetic flavoring agents (saccharin, aspartame, and the like) may be advantageously used. A proportion of the natural carbohydrate is generally about 1 to 20 g, and preferably about 5 to 12 g per 100 mL of the composition of the present invention.

In addition to the above-mentioned ingredients, the food composition of the present invention may further contain various nutrients, vitamins, minerals (electrolytes), flavors such as synthetic flavors and natural flavors, coloring agents and fillers (cheese, chocolate, or the like), pectic acid and salts thereof, alginic acid and salts thereof, organic acids, protective colloidal thickening agents, pH adjusting agents, stabilizing agents, preservatives, glycerin, alcohol, carbonizing agents as used in carbonated beverages, and the like. These components may be used independently or in combination. Although a proportion of such additives is not so important, the proportion is generally selected from a range of 0 to about 20 parts by weight per 100 parts by weight of the composition of the present invention.

In addition, the present invention provides a method for preventing or treating chronic allograft dysfunction, comprising a step of administering, to a subject in need of treatment, the pharmaceutical composition according to any one of claims 1 to 6 so as to prevent or treat chronic allograft dysfunction.

In an embodiment of the present invention, the pharmaceutical composition is administered to the subject in an amount of 0.0001 to 50 mg/kg or 0.001 to 50 mg/kg per day.

In addition, the present invention provides a use of the pharmaceutical composition according to any one of claims 1 to 6, for the prevention or treatment of chronic allograft dysfunction.

In an embodiment, the pharmaceutical composition is administered to a subject in need of treatment in an amount of 0.0001 to 50 mg/kg or 0.001 to 50 mg/kg per day.

In addition, the present invention provides a food composition for preventing or ameliorating chronic allograft dysfunction, comprising a step of causing a subject in need of amelioration to ingest the food composition according to any one of claims 7 to 12 so as to prevent or ameliorate chronic allograft dysfunction.

In an embodiment of the present invention, the food composition contains bisphosphonate in an amount of 0.01 to 15% by weight of the total food weight. In another embodiment of the present invention, the food composition contains bisphosphonate in an amount corresponding to a proportion of 0.02 to 10 g, and preferably 0.3 to 1 g based on 100 mL.

In addition, the present invention provides a use of the food composition according to any one of claims 7 to 12, for the prevention or amelioration of chronic allograft dysfunction.

In an embodiment of the present invention, the food composition contains bisphosphonate in an amount of 0.01 to 15% by weight of the total food weight. In another embodiment of the present invention, the food composition contains bisphosphonate in an amount corresponding to a proportion of 0.02 to 10 g, and preferably 0.3 to 1 g based on 100 mL.

Advantageous Effects of Invention

The composition for preventing or treating chronic allograft dysfunction, comprising bisphosphonate, according to the present invention has an excellent prophylactic and/or therapeutic effect on chronic allograft dysfunction caused by a gradual decrease in the function of a transplanted tissue or organ which occurs after tissue or organ transplantation surgery, and thus is expected to be able to remarkably increase a long-term survival after transplantation surgery.

BRIEF DESCRIPTION OF DRAWINGS

FIG. 1 illustrates results obtained by identifying an average survival probability (~300 months) for the entire bisphosphonate experimental group according to an embodiment of the present invention.

FIG. 2 illustrates results obtained by identifying a long-term survival probability for an alendronate-administered group according to an embodiment of the present invention.

FIG. 3 illustrates results obtained by identifying a long-term survival probability for an etidronate-administered group according to an embodiment of the present invention.

FIG. 4 illustrates results obtained by identifying a long-term survival probability for a pamidronate-administered group according to an embodiment of the present invention.

FIG. 5 illustrates results obtained by identifying a long-term survival probability for a risedronate-administered group according to an embodiment of the present invention.

FIG. 6 illustrates results obtained by identifying an average survival probability for etidronate-, ibandronate-, and pamidronate-administered groups according to an embodiment of the present invention.

DETAILED DESCRIPTION OF INVENTION

The present invention relates to a composition for preventing or treating chronic allograft dysfunction, comprising bisphosphonate which is used as a therapeutic agent for osteoporosis. The composition for preventing or treating chronic allograft dysfunction, comprising bisphosphonate, according to the present invention has an excellent prophylactic and/or therapeutic effect on chronic allograft dysfunction caused by a gradual decrease in the function of a transplanted tissue or organ which occurs after tissue or organ transplantation surgery, and thus is expected to be able to remarkably increase a long-term survival after transplantation surgery.

Hereinafter, the present invention will be described in more detail by way of examples. These examples are only for describing the present invention in more detail, and it will be apparent to those skilled in the art that according to the gist of the present invention, the scope of the present invention is not limited by these examples.

EXAMPLES

Example 1: Identification of Role of Bisphosphonate in Chronic Allograft Dysfunction In order to identify a role of bisphosphonate in chronic allograft dysfunction, among 4,000 patients who had undergone kidney transplantation (KT) at the Yonsei University Health System from April 1979 to June 2016, studies were conducted on 3,939 patients, except for those for whom bisphosphonate was used before transplantation and data was lost. Among the patients to be studied, 3,022 patients (control group) were not subjected to bisphosphonate, and the remaining 917 patients were subjected to bisphosphonate one year after the surgery. A renal function test (glomerular filtration rate; GFR) was performed on the patients at the time of being subjected to bisphosphonate, and 866 patients with a test result of 30 mL/min/1.73 $m^2$ or higher were designated as an experimental group. Graft survivals of the control and experimental groups were analyzed using propensity score matching (PSM). All statistical analyses of the examples were performed using IBM PSS statistics ver. 21 (IBM Korea Corporation, Seoul, Korea) and MedCalc Ver. 11.6 (MedCalc Software). "$p<0.05$" was determined as significant. As bisphosphonates, risedronate (risedronic acid), ibandronate (ibandronic acid), etidronate (etidronic acid), alendronate (alendronic acid), and pamidronate (pamidronic acid) were used. Risedronate was used for 559, ibandronate for 16, etidronate for 13, alendronate for 245, and pamidronate for 33. Dosage and frequency of administration were used according to respective conventional administration methods. The results are illustrated in FIGS. 1 to 6.

As illustrated in FIG. 1, it was identified that until 100 months, no large difference in survival probability is observed between the experimental group to which bisphosphonate has been administered and the control group to which no bisphosphonate is administered; and after that, a difference in survival probability gradually increases therebetween. From this, it was found that administration of bisphosphonate has little effect on a short-term survival probability, but results in a remarkable increase in survival probability over the long term.

In addition, as illustrated in FIGS. 2 to 6, even in the results obtained by identifying long-term survival probabilities with administration of the respective bisphosphonates, it was identified that no difference is observed in the short-term survival probability, but a remarkable difference is observed in the long-term survival probability.

From the above results, it was found that in a case where bisphosphonate, which has been previously used as a therapeutic agent for osteoporosis, is administered to patients who have undergone kidney transplantation, the incidence of chronic allograft dysfunction is remarkably decreased, and thus a long-term survival of kidney transplant patients can be remarkably increased, which makes it possible to identify that bisphosphonate can be used for the prevention or treatment of chronic allograft dysfunction.

Although the present invention has been described in detail with respect to specific parts, it will be apparent to those skilled in the art that such particular description is only for preferred embodiments and does not limit the scope of the present invention. Therefore, the substantial scope of the present invention will be defined by the appended claims and equivalents thereof.

INDUSTRIAL APPLICABILITY

The present invention relates to a composition for preventing or treating chronic allograft dysfunction, comprising bisphosphonate which is used as a therapeutic agent for osteoporosis.

The invention claimed is:

1. A method for treating chronic allograft dysfunction, comprising a step of administering, to a subject in need thereof, a pharmaceutical composition comprising bisphosphonate as an active ingredient,
   wherein the bisphosphonate is any one selected from the group consisting of risedronate (risedronic acid), ibandronate (ibandronic acid), etidronate (etidronic acid), alendronate (alendronic acid), and pamidronate (pamidronic acid),
   wherein the chronic allograft dysfunction is caused by transplantation of kidney, and
   wherein the method increases a long-term-survival of subject after transplantation surgery.

2. The method according to claim 1,
   wherein the bisphosphonate is used for the treatment of osteoporosis.

3. The method according to claim 1,
   wherein the pharmaceutical composition is in the form of suspensions, powders, granules, tablets, sustained release preparations, injections, ointments, or eye drops.

4. The method according to claim 1,
   wherein the pharmaceutical composition is administered to the subject in an amount of 0.0001 to 50 mg/kg or 0.001 to 50 mg/kg per day.

* * * * *